United States Patent [19]

Aschinger et al.

[11] 4,304,123
[45] Dec. 8, 1981

[54] MICRO HARDNESS TESTER

[76] Inventors: Hubert Aschinger, Kraftgasse 65, St. Poelten, Austria, A-3105; Ekkehard Kubasta, Zwinzstrasse 4-6/1/21, Vienna, Austria, A-1160; Alfred Wagendristel, Aspettenstrasse 34, Perchtoldsdorf, Austria, A-2380; Herwig Bangert, RudolfWaisenhorng. 45, Vienna, Austria, A-1235; Elmar Tschegg, Boltzmanngasse 9, Vienna, Austria, A-1090

[21] Appl. No.: 112,477

[22] Filed: Jan. 16, 1980

[30] Foreign Application Priority Data

Jan. 18, 1979 [AT] Austria .................................. 361/79

[51] Int. Cl.³ .............................................. G01N 3/42
[52] U.S. Cl. .................................... 73/81; 73/83
[58] Field of Search .............................. 73/78, 81, 83

[56] References Cited

U.S. PATENT DOCUMENTS

| | | | |
|---|---|---|---|
| 2,422,634 | 6/1947 | Riepert et al. | 73/81 |
| 2,804,769 | 9/1957 | Clark | 73/81 |
| 3,564,908 | 2/1971 | Fischer | 73/81 |
| 3,693,417 | 9/1972 | Fritz et al. | 73/81 |
| 4,094,188 | 6/1978 | Bellouin et al. | 73/81 |

FOREIGN PATENT DOCUMENTS 587363  1/1978  U.S.S.R. .................................. 73/81

*Primary Examiner*—James J. Gill
*Attorney, Agent, or Firm*—Townsend and Townsend

[57] ABSTRACT

The invention relates to a micro hardness tester (durometer) having a penetration body such as a point or the like penetrating into a sample under load. An electrical means is provided for loading the penetration body and the bearing force of the penetration body is convertible into electrical signals for the purpose of measuring said force. The invention is characterized in that the penetration body is fixed to an arm or spring arranged on a mounting element which spring or arm also carries at least one strain gauge or a micro dynamometer cell for measuring the bearing force of the penetration body.

11 Claims, 20 Drawing Figures

MICRO HARDNESS TESTER

The invention relates to a micro hardness tester (durometer) having a penetration body, such as a point or the like, penetrating into a sample under load, an electrical means being provided for loading the penetration body and the bearing force of the penetration body being convertible into electrical signals for the purpose of measuring. The micro hardness testers now in use basically permit measurement of the micro hardness of a sample, although bearing pressures of less than $1 \times 10^{-2}$ N cannot be achieved at the construction principles applied up to now.

It is the object of the invention to provide a micro hardness tester for testing loads within the range of about $5 \times 10^{-5}$ to $1 \times 10^{-1}$ N. This hardness tester is particularly intended for assembling into commercially available electronic scanning microscopes, should be operable within these without necessitating the provision of additional adjusting or actuating means and allow observation of the penetrator during the test and examination of the penetration mark (impression) at full utilization of the possibilities of the microscope. Due to its suitability for precise adjustment, its extremely low bearing pressures and the resulting negligible penetration depths of the penetrator, the testing device proposed should be particularly well suited for testing the mechanical properties of thin layers, of powder particles and of finely structured solid body surfaces. Its construction should be simple and fail-safe.

This object is achieved according to the invention by fixing the penetration body on an arm arranged on a mounting element, with at least one elongation strip chart (strain gauge) or micro dynamometer cell being fixed to the arm for measuring the bearing force of the penetrator.

The invention is described in detail by means of the following embodiments, including a description of the advantages characterized in the sub claims.

Figure 1A:
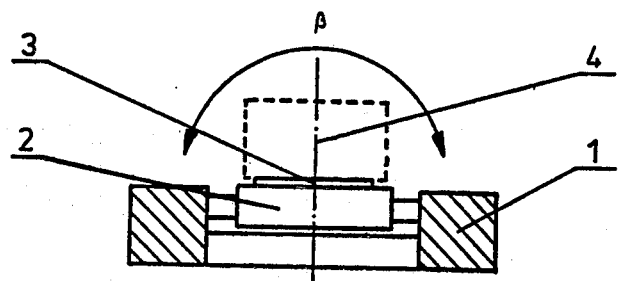
FIGS. 1A and 1B are cross-sectional and plan views of the sample support of an electronic scanning microscope, the support being operable from the outside by adjusting or actuating means, with the moving possibilities x, y, α, β of the support indicated by means of arrows.
Figure 1B:
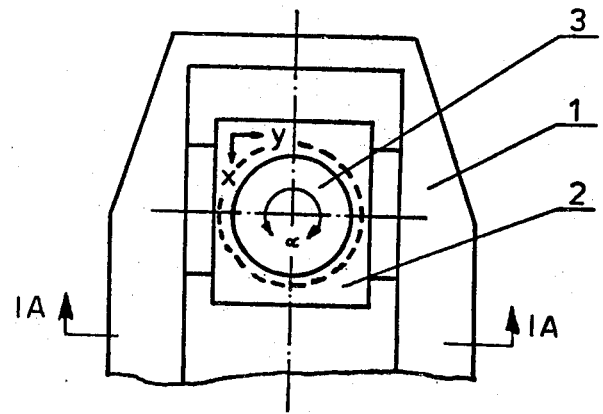

The moving possibilities of the support 2 are indicated by means of arrows x, y, α, β in FIGS. 1A and 1B. The support frame 1 is tiltable to form angle β, the sample support 2 is displaceable in directions x and y. The sample support platform 3 itself is rotatable by 360° (angle α). The sample carrier 4 with the sample is fastened to platform 3.

Figure 2A:
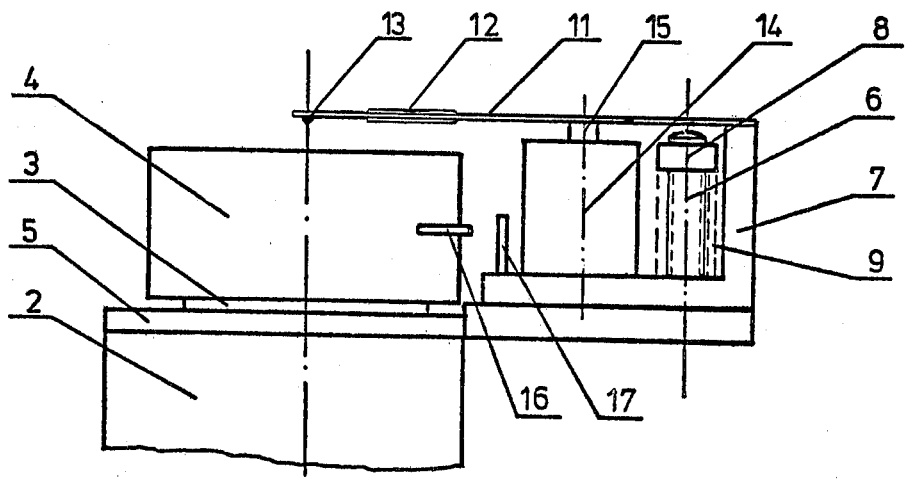
FIGS. 2A and 2B are side and plan views of a micro hardness tester mounted on the sample support with a blade spring or spring arm and elongation strip charts.
Figure 2B:
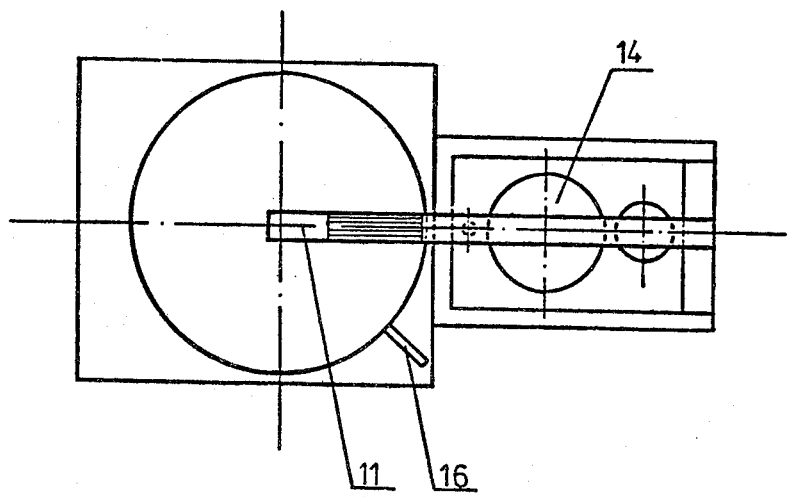
Figure 3A:
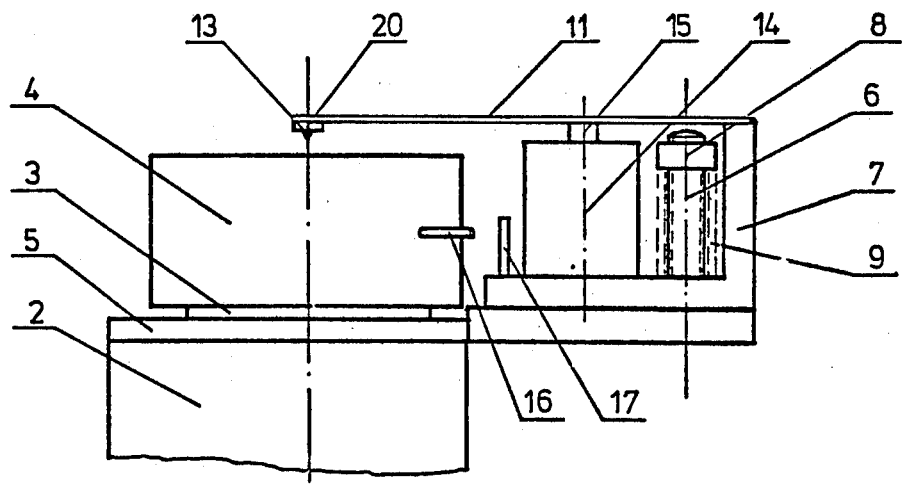
FIGS. 3A and 3B are side and plan views of a micro hardness tester mounted on the sample support with a blade spring or spring arm and micro dynamometer cell.
Figure 3B:
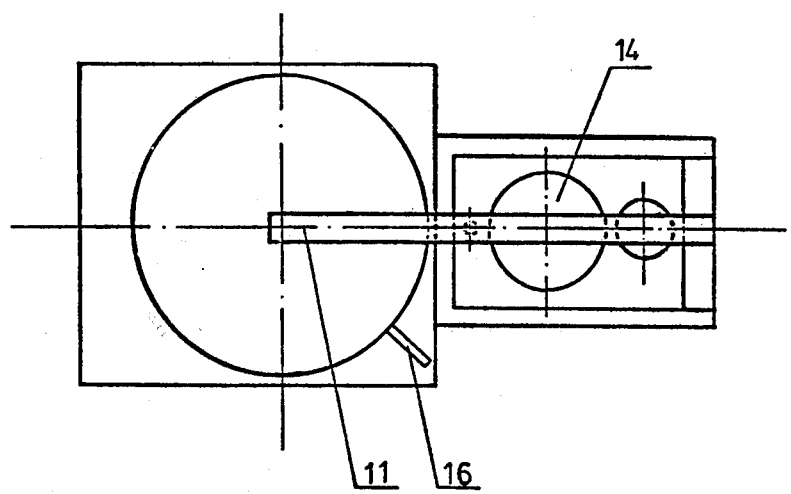

A mounting or base plate 5 (FIGS. 2A and 2B) of the hardness tester is fixed to the sample support 2. The micro hardness tester is arranged on plate 5 rotatably around a pin 6 via a slipper clutch. An adjusting nut 8 with pressure spring 9 serves for adjustment of the desired sliding friction between mounting plate 5 and mounting element 7. A blade spring 11 with at least one, preferably two, glued-on elongation strain gauges 12, a penetrator 13, for instance a diamond point, and an iron core 15 is fixed in an easily releasable manner to the upper end of the mounting element 7. Further arranged on the mounting element 7 are a shielded coil 14 (for instance a piezoelectric motor) and a stop pin 17. An adjusting pin 16 is mounted on the rotatable sample carrier 4.

The sample is fixed in a conventional manner to the sample carrier 4, placed into the microscope and the desired part of the sample is placed in center of image by the adjusting or actuating means x, y. For positioning the penetrator 13 above the desired sample spot, the stop pin 17 and the adjusting pin 16 are placed into contact by rotation of the sample platform 3 by angle α; at further rotation by α, the micro hardness testing device is moved on the mounting plate 5 and the penetrator 13 can thus be placed in center of image. After resetting the α-actuator to its original position, the penetrator 13 and the desired sample spot are placed one above the other and in center of image. Tilting by angle β allows a suitable angle of view onto the sample. By means of the controllable coil current in the coil 14, the penetrator 13 is approached to and finally placed onto the sample surface as a result of the movement of the iron core in the magnetic field of the coil 14 (for instance by means of a variable voltage on the piezoelectric motor). The first flexion of spring 11 occurs immediately after setting of the penetrator point. This flexion is recorded by means of the elongation strip chart and thus represents the zero point of the test load. The electrical signal emitted by the elongation strip chart also represents a measure for the further test load applied electromagnetically (or piezoelectrically) which results in a further flexion of the spring 11. Once the penetration (impression) is completed, the coil current or voltage is reduced, the penetrator 13 lifts off from the sample surface and the impression can be examined, measured and recorded without further adjustment. As a result of the moving possibilities of the sample in relation to the penetrator 13 by means of the actuators x, y and α, any given spot in a sample surface of about 1.5 cm² can be selected for hardness testing. There is also the more elaborate possibility of arranging further actuators for adjusting and pivoting of the penetrator in relation to the sample or the use of the existing x and y actuators.

Following a non-recurring adaptation of the sample support 2, assembling of the micro hardness tester takes only a few minutes: the mounting element 7 is fixed to the sample support 2 by means of screws or a specific guide means and the electrical connections for coil current or voltage and the signal lines of the strain gauges 12 are established by means of plug couplings via a vacuum duct. No pre-adjustment of the penetrator 13 is required.

Exchanging of samples is very simple as the distance between sample surface and penetrator 13 amounts to about 3 to 4 mm in the inactive position of spring 11 (currentless coil).

Calibration of the electrical test load indication by means of the strain gauges 12 on a deflection spring can be effected, for instance, by means of a set of weights or on a microscale at a precision of $\pm 5 \times 10^{-5}$ N, a change of the measuring range is effected by exchanging blade spring 11. For major changes of the measuring range, coil 14 and/or iron core 15 (or piezoelectric motor) can be exchanged. Depending upon the type of test, the penetrator 13 can have the shape of a pyramid, conus, sphere or edge. It is attached to the end of the spring blade by means of a screw connection and thus easily exchangeable. If desired, coil 14 can be subdivided into a coil for coarse adjustment and a coil for fine adjustment of the current load.

Figure 4A:
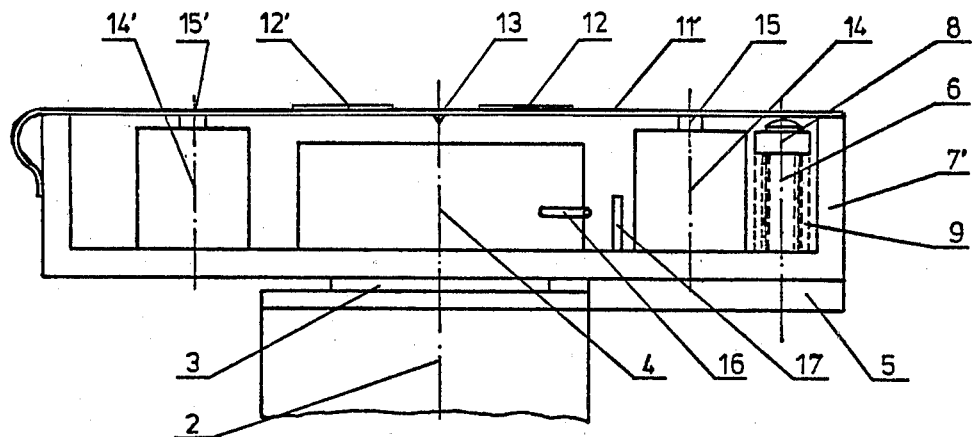
FIGS. 4A and 4B are side and plan views of a micro hardness tester mounted on the sample support with guided spring arm or blade spring and elongation strip charts.
Figure 4B:
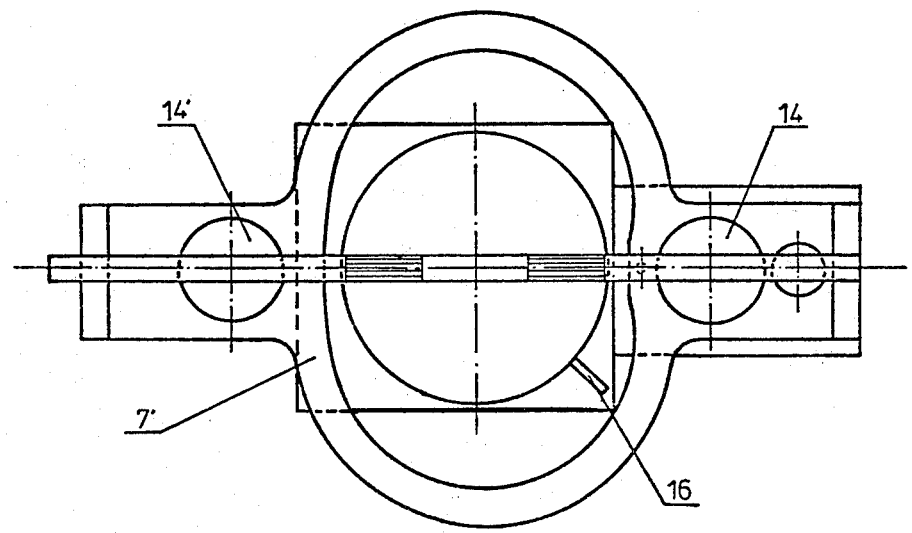
Figure 5A:
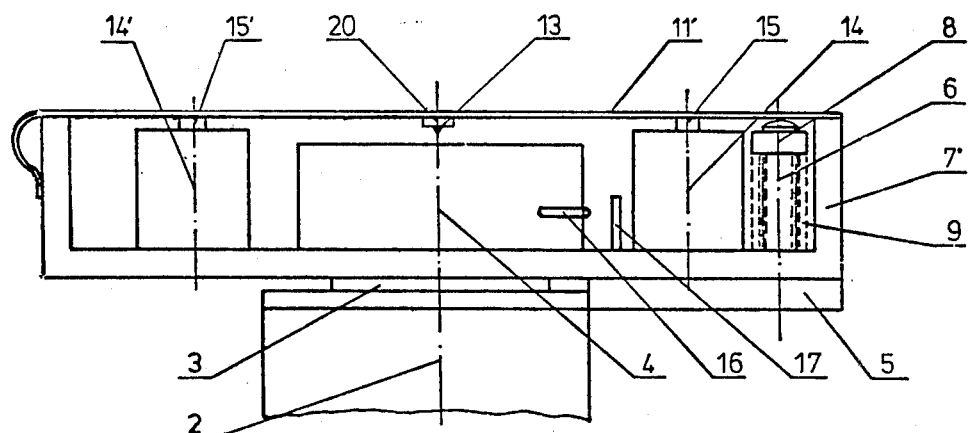
FIGS. 5A and 5B are side and plan views of a micro hardness tester mounted on the sample support with guided spring arm or blade spring and micro dynamometer cell.
Figure 5B:
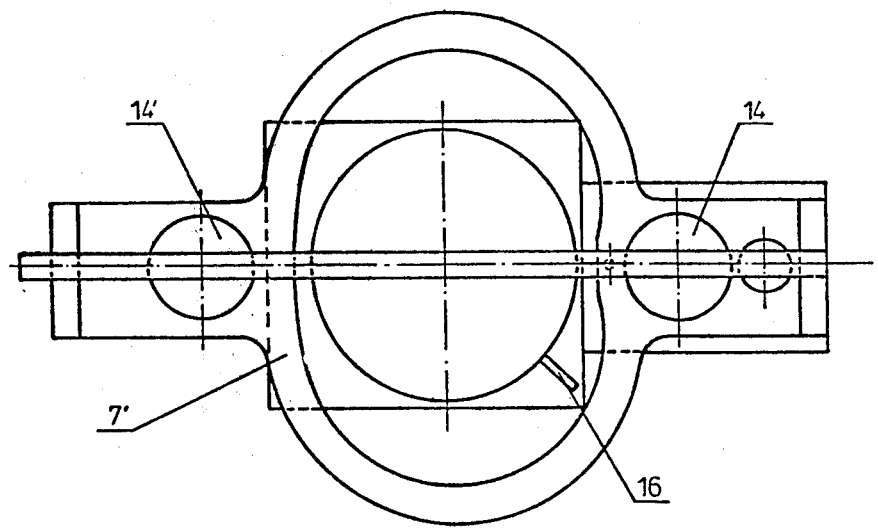

FIGS. 4A and FIG. 4B show a micro hardness tester in which the spring is positioned on either side of the sample carrier 4 to avoid deviation of the penetrator 13 as a result of the flexion of the spring during penetration. A further coil 14' with a further core 15' (or piezoelectric motor) fixed to spring 11' is provided on the mounting element 7'. Two further strain gauges 12' serve for improving the precision of measuring. The signals emitted by the strain gauge 12' can be evaluated separately or jointly (series connection) with those of the elongation strip chart 12. The arrangement as a whole is pivotable around pin 6 of the slipper clutch so as to be able to adjust the penetrator, as initially indicated, by means of the α-actuator, the x and y actuators or additional x and y actuators above the sample surface.

Figure 6A:
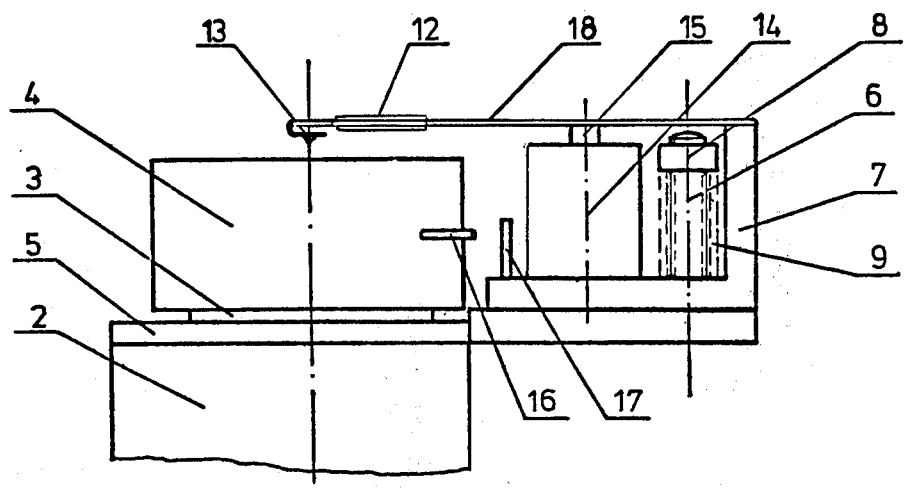
FIGS. 6A and 6B are side and plan views of a micro hardness tester mounted on the sample support with spring arm or blade spring bent in U-shape and elongation strip charts.
Figure 6B:
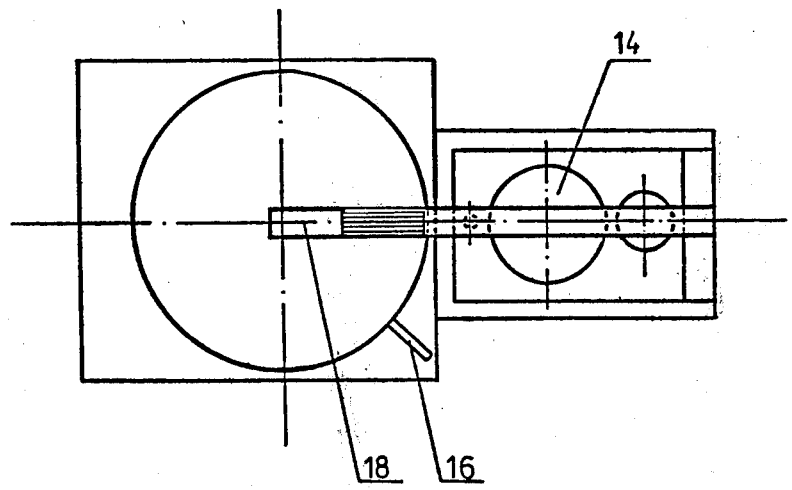
Figure 7A:
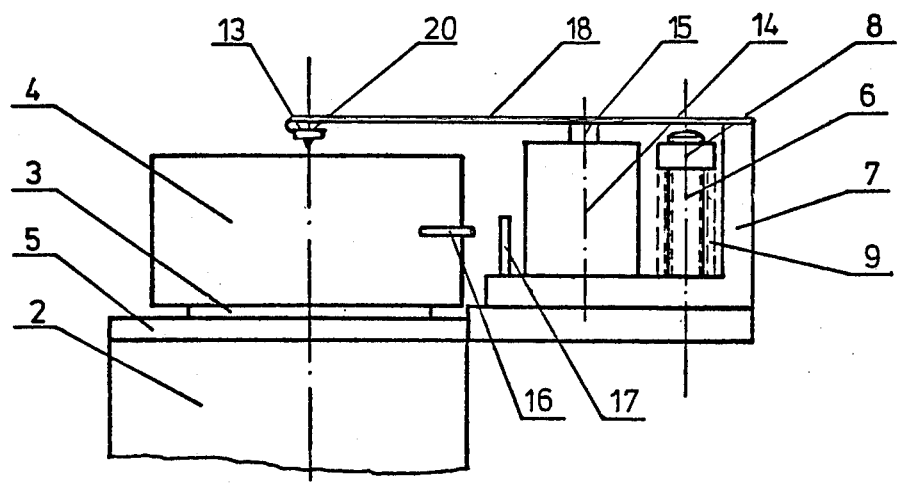
FIGS. 7A and 7B are side and plan views of a micro hardness tester mounted on the sample support with spring arm or blade spring bent in U-shape and micro dynamometer cell.
Figure 7B:
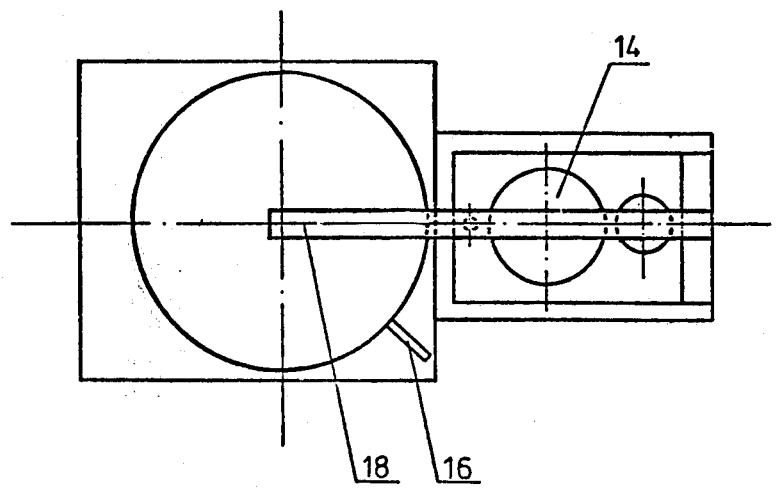

FIGS. 6A and 6B show spring 18 bent U-shaped at the end and carrying the penetrator 13 on the bent leg. Deviation of the penetrator can be avoided by appropriate selection of material, length and stiffness of spring and leg. In this embodiment, as well, spring 18 can be approached to the sample by means of coil 14 and iron core 15 or a piezoelectric motor. Advantageously, two elongation strip charts facing one another whose signals can be evaluated in a bridge circuit are again provided.

Figure 10A:
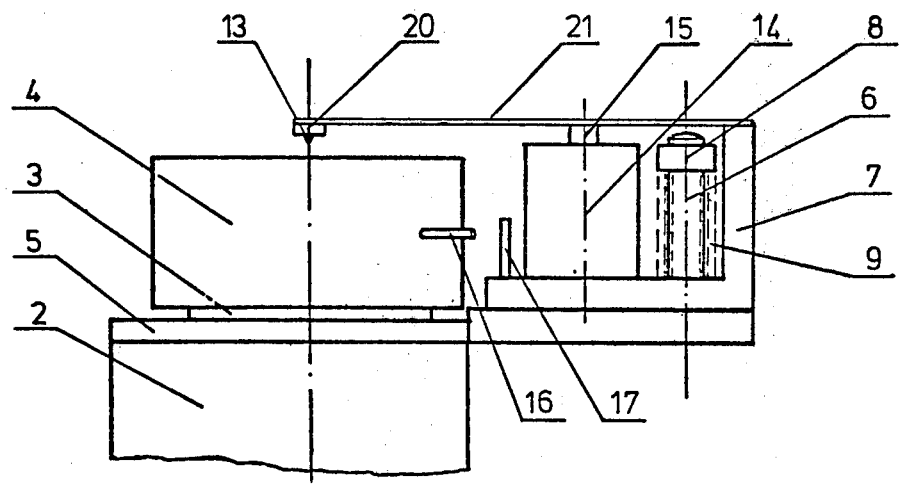
Figure 10B:
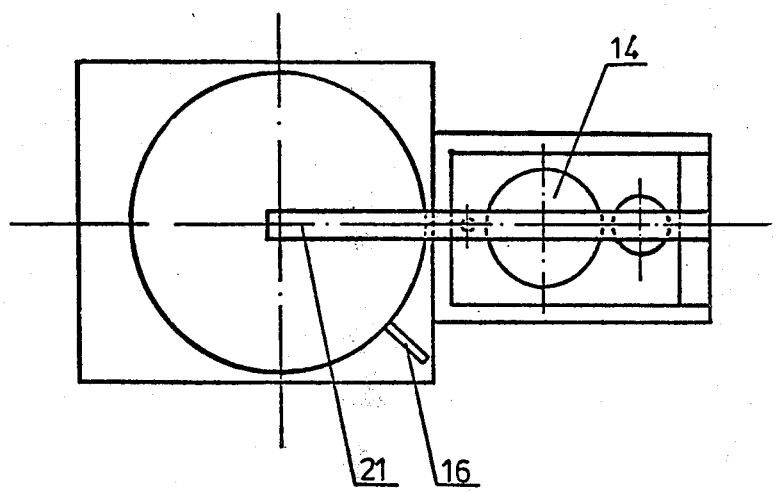

FIG. 10 shows a micro hardness tester having a rigid, pivotably supported arm 21 at whose end a micro dynamometer cell 20 carrying the penetrator 13 and emitting electrical signals corresponding to the bearing force is fixed. The rigid arm 21 can be approached to the sample surface by means of coil 14 and core 15 or a piezoelectric motor. The principle of measuring force by means of a micro dynamometer cell can also be applied to a micro hardness tester of the variants initially described having a flexible arm instead of the strain gauge (FIGS. 3A, 3B, 5A, 5B, 7A and 7B). The penetrator can be screwed, glued or otherwise fixed to the spring or micro dynamometer cell.

Figure 8A:
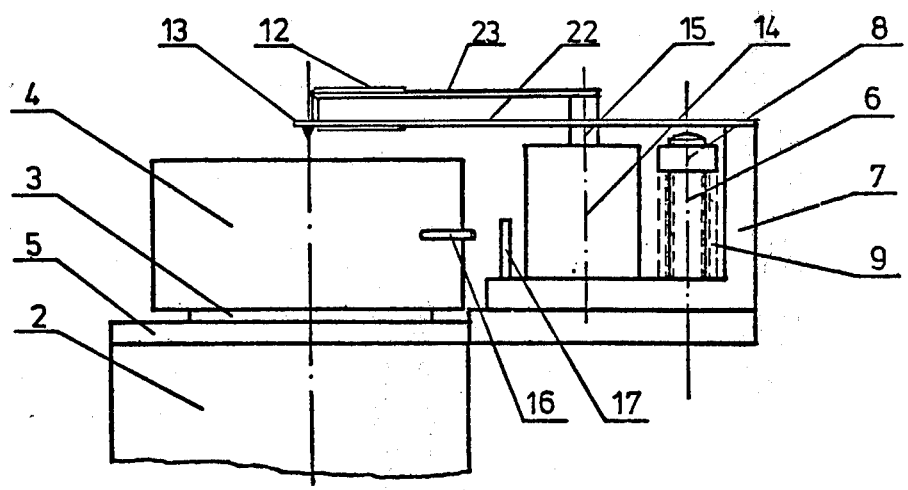
FIGS. 8A and 8B are side and plan views of a micro hardness tester mounted on the sample support with parallel spring arms or blade springs and elongation strip charts.
Figure 8B:
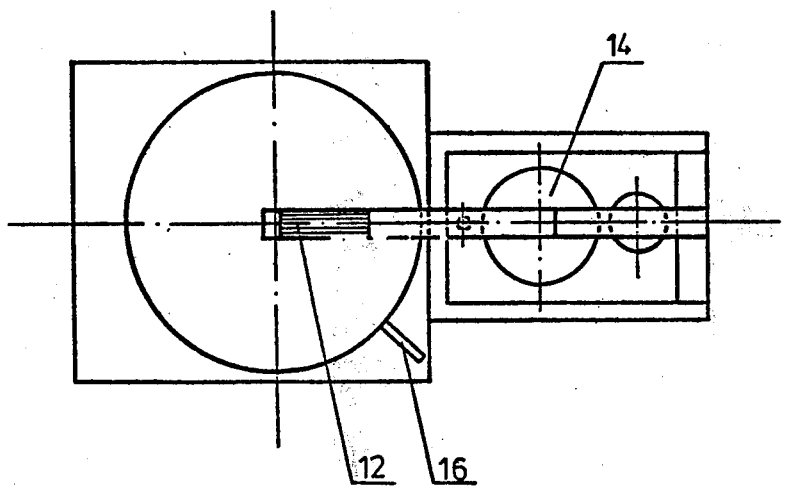
Figure 9A:
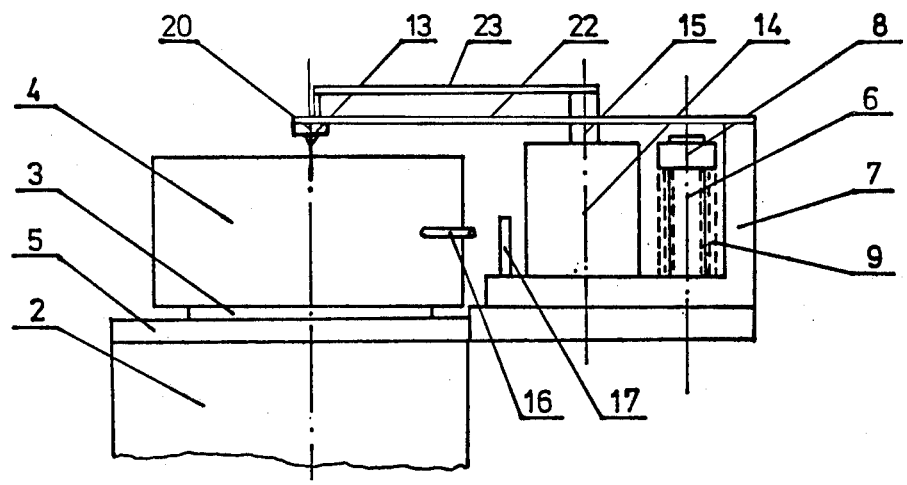
FIGS. 9A and 9B are side and plan views of a micro hardness tester mounted on the sample support with parallel spring arms or blade springs and micro dynamometer cell and FIGS. 10A and 10B are side and plan views of a micro hardness tester mounted on the sample support with pivotably supported arm.
Figure 9B:
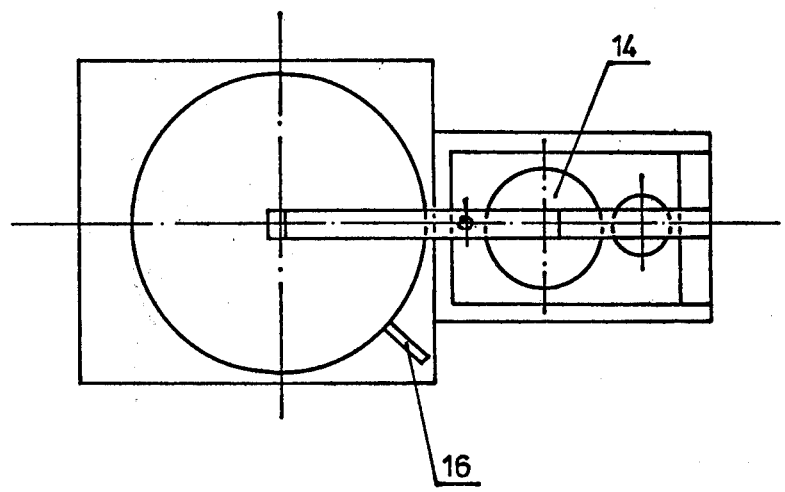

FIGS. 8A and 8B show an alternative embodiment of the flexible arm by using two parallel springs 22, 23 connected in the manner of a parallelogram guide which again prevents deviation of the penetrator 13 during penetration. The application of force can be effected by means of an electromagnet 14 (or a piezoelectric motor), the measuring of force by means of strain gauge 12 or a dynamometer cell 20 (FIG. 9).

What is claimed is:
1. A micro hardness tester comprising:
   a penetration body for penetration into a sample under load;
   a spring arm having first and second ends and along which the penetration body is mounted;
   an electrical means for controllably loading the spring arm at a loading position on the spring arm, the loading position being spaced apart from the penetration body and from the first and second ends of the spring arm;
   a mounting element to which the spring arm is attached at the first end, the mounting element being pivotably arranged on a sample carrier that is mounted for rotation about vertical and horizontal axes and moveable along two perpendicular horizontal axes to permit displacement of the sample in horizontal directions x and y, rotation of the sample and tilting of the sample;
   means, mounted to the arm, for indicating the load on the spring arm thereby indicating the bearing force of the penetration body on the sample.

2. A micro hardness tester according to claim 1 wherein the penetration body is mounted medially along the spring arm and including means for guiding the second end of the spring arm along the mounting element.

3. A micro hardness tester according to claim 1 wherein the penetration body is mounted to the second end of the spring arm.

4. A micro hardness tester according to claim 3 wherein the second end of the spring arm being bent backwards in a U-shape.

5. A micro hardness tester according to claim 3 wherein the spring arm further comprises a second, parallel spring member connected to said spring arm in the manner of a parallelogram guide to minimize deviation of the penetration body.

6. A micro hardness tester according to claim 5 wherein said spring member has outer and inner ends and is connected at the outer end to and spaced apart from the second end of the spring arm and is connected at the inner end to and spaced apart from the spring arm at the loading position.

7. A micro hardness tester according to claim 1 wherein the carrier includes a mounting plate, the mounting element being clutchably coupled to the mounting plate.

8. A micro hardness tester according to claim 7, wherein a stop pin is provided on the pivotable mounting element and an adjusting pin is provided on the carrier with the adjusting pin abutting the stop pin and the adjusting pin pivoting the stop pin and thus the spring arm attached to the mounting element at further rotation of the carrier.

9. A micro hardness tester according to claim 1 wherein the electrical loading means is an electromagnetic coil.

10. A micro hardness tester according to claim 9, wherein the electromagnetic coil includes a coarse adjustment coil and a fine adjustment coil.

11. A micro hardness tester according to claim 1 wherein the electrical loading means is a piezoelectric motor.

* * * * *